United States Patent [19]

Escalona et al.

[11] Patent Number: 5,536,419

[45] Date of Patent: Jul. 16, 1996

[54] PROCEDURE FOR EXTRACTION OF POLYHYDROXYALKANOATES FROM HALOPHILIC BACTERIA WHICH CONTAIN THEM

[75] Inventors: Antonio M. Escalona, Madrid; Francisco R. Varela; Antonio M. Gomis, both of Alicante, all of Spain

[73] Assignee: Repsol Quimica S.A., Madrid, Spain

[21] Appl. No.: 234,325

[22] Filed: Apr. 28, 1994

[30] Foreign Application Priority Data

Apr. 29, 1993 [ES] Spain .................................. P9300914

[51] Int. Cl.$^6$ .................................................. B01D 37/00
[52] U.S. Cl. ........................ 210/767; 210/787; 134/29; 435/135; 435/146; 435/170; 435/252.1; 435/259
[58] Field of Search ................................ 435/135, 170, 435/146, 259, 253.1, 252.1; 134/29, 30; 210/787, 772, 806, 767

[56] References Cited

U.S. PATENT DOCUMENTS

| | | | |
|---|---|---|---|
| 3,871,957 | 3/1975 | Mohan et al. | 210/611 |
| 3,933,591 | 1/1976 | Dasek et al. | 435/259 |
| 4,910,145 | 3/1990 | Holmes et al. | 435/259 |
| 5,135,859 | 8/1992 | Witholt et al. | 435/146 |
| 5,138,029 | 8/1992 | Nishioka et al. | 435/135 |

FOREIGN PATENT DOCUMENTS 292888  11/1988  European Pat. Off. .............. 210/806

OTHER PUBLICATIONS

Thomas D. Brock, et al., Biology of Microorganisms, 4th edition, 1984, pp. 254–255.
Applied and Environmental Microbiology, Aug. 1990, pp. 2517–254, Rodriquez–Valera et al.
The Microbial World, 2nd ed., ©1957, 1963, pp. 357–358 Stanier et al.
Fundamentals of Microbiology, 9th ed., pp. 286, 426 Frobisher et al.

*Primary Examiner*—Robert A. Dawson
*Assistant Examiner*—Kenneth M. Jones
*Attorney, Agent, or Firm*—Ladas & Parry

[57] ABSTRACT

A procedure for the extraction of polyhydroxyalkanoates from halophilic bacteria which contain them, using lysis or rupture of halophilic cells (for example, of the halobacteria type) which develop in media with high salt concentrations, by concentration by centrifugation, and then dilution-resuspension in a medium with low salt concentration, for example, fresh or distilled water, and then centrifugation, sedimentation, or filtration of the suspension obtained.

17 Claims, No Drawings

PROCEDURE FOR EXTRACTION OF POLYHYDROXYALKANOATES FROM HALOPHILIC BACTERIA WHICH CONTAIN THEM

This invention concerns a process for extraction of polyhydroxyalkanoates, hereinafter referred to as "PHA", produced from cells of halophilic bacteria.

PHAs are accumulated intracellularly by many bacteria in the form of granules. The use of these polymers as thermoplastics requires their separation from the rest of the cellular materials with an adequate level of purity. For this, numerous methods have been described based on the use of solvents and selective precipitants, which methods extract the polymer PHA from the complex mixture which constitutes the cellular biomass by means of a process of dissolution and precipitation.

U.S. Pat. No. 3,107,172 proposes spray-drying the cells and using the resultant material directly for casting. Other patents perform the extraction and purification of the polymer using solvents in which PHA is soluble and can thus lixiviate the PHA from the rest of the cellular material. For example, British Patent 7906076 proposes drying the aqueous suspension of bacteria in a current of gas at a high temperature and using mixtures of solvents (dichloroethane, chloroform, etc.) and non-solvents (acetone and methanol) to recover the purified polymer. Other procedures consist in concentrating the suspension by centrifugation and treating it with acetone to dry and rupture the cells. Then, the polymer is extracted with an appropriate solvent (pyridine— U.S. Pat. No. 3,036,959 or with a mixture of dichloromethane-ethane—U.S. Pat. No. 3,044,942). Then, it is necessary to recover the polymer and, finally, the solvent, usually by rectification (for example, European Patent 84302508.1). U.S. Pat. No. 3,275,610 describes a method whereby the cells suspended in water are subjected to the action of a vibrating field to lixiviate the PHA. Once the cells are ruptured, the resultant mass is centrifuged and dried. Next, it is treated with a solvent (chloroform) to purify the PHA. This operation normally requires high energy consumption. U.S. Pat. No. 4,101,533 proposes using hot cyclic esters of carbonic acid, from which the polymer precipitates upon cooling, avoiding the steps of solvent recovery. It is also possible to extract the PHA directly from the aqueous suspension of the cells without the need to remove the water from it by centrifugation or drying with gas with the direct use of certain solvents (chloroform, dichloromethane, dichloroethane) although at times in cells with hard walls, a prior grinding process is needed to rupture the cells. This process requires control of the extraction conditions to avoid the formation of a relatively stable emulsion due to the action of the solvent on the lipids and pigments, which makes purification difficult, leaving the PHA contaminated.

In any case, the process for obtaining PHA is expensive and involves the use of large quantities of organic solvents. These solvents must be recovered and reused in the process to make it cost-effective.

The present procedure is applicable to the extraction of granules of PHA produced by halobacteria and other halophilic bacteria. It is based on the weakness of the cell envelopes of these microorganisms when they are exposed to low concentrations of salts, for example, in fresh water; under these conditions the cells of halophilic bacteria lyse (rupture), releasing all the cell components into the medium. Since the granules of PHA are of considerable size and density, they can be recovered from the suspension of cells once lysed, by centrifugation at low speed, sedimentation, filtration, etc. It is this property of halophilic bacteria such as Haloferax Mediterranei (U.S. Pat. No. 890,347) which makes possible the present patent, where water and low concentrations of detergents are used to obtain the polymer with high yields and levels of purity, in both continuous and discontinuous processes.

Thus, it is possible to obtain a sediment of PHA granules with minimum lipid and protein contamination. To eliminate these contamination residues, the sediment may be washed once or a plurality of times with detergents which break down proteins, for example, sodium dodecyl sulfate (SDS) (the detergents may be anionic, cationic, nonionic, or amphoteric). After a variable number of washings with the detergent and finally with water, the material is collected, and a fine powder made up of PHA with adequate purity to be used directly in polymer processing machines is obtained.

With this procedure the need to dry the aqueous suspension of the bacteria and the use of organic solvents are eliminated, significantly simplifying handling and eliminating the need to use solvents and to recycle them. Thus, the product extraction step becomes significantly less expensive, making the possibility of industrial-scale fabrication much more cost-effective and attractive.

The first step in this procedure is the elimination of the saline medium in which the bacteria grow. For this, it is necessary to concentrate the suspension of the bacteria as much as possible. For example, for halobacteria, NaCl at 20 to 25 wt.-% and various magnesium salts are used. To cause lysis of the cells, it is necessary to reduce the concentration of these salts in the medium which surrounds the cells to less than 0.5% for the NaCl and to less than 0.1% for the magnesium; otherwise, the lysis would not be effective. For this, once the medium has been eliminated, it is necessary to resuspend the cells in a quantity of water large enough that the concentration of salts reaches the level indicated. To assure lysis of all the cells in the least possible time, in this step it is possible to already add a detergent which causes dissolution of the cell envelopes, bile salts, such as taurocholate and dexicholate [sic: ?deoxycholate], which are very effective in producing lysis, and a cation complexing agent. On the other hand, the use of an excessive amount of water increases the expense of the extraction by raising the consumption of water and/or detergent and increases the time and consumption of energy for centrifugation and/or sedimentation filtration.

To activate the lysis of the cells, it is also possible to heat the suspension, for example, to 50° to 60° C. for 20 to 30 min. It is also possible to subject the cells to other systems of mechanical rupturing to accelerate the lysis, including intense agitation, sudden depressurization, freezing and thawing, etc.

After obtaining the suspension of granules free of whole cells and cell residues of significant size, sedimentation or low-speed centrifugation is begun, recovering the PHA granules with a high level of purity. For this step, it is important that the starting culture medium be as free as possible of particulate matter, because if present it would be collected with the granules, contaminating the final product.

The sediment containing the granules usually presents lipid and protein contamination. This contamination can be reduced to traces with one or a plurality of washing operations using water and a detergent which dissolves proteins, such as SDS. The purity of the preparation can be monitored visually by the loss of the pink color which characterizes the sediment in the initial steps, and which results from the presence of contaminants from the cell membrane of the microorganism and of whole cells which have not lysed yet.

The detergents to be used may be anionic (sodium or potassium salts of linear fatty acids, linear alkylbenzene sulfonate (LAS), paraffin sulfonates, α-olefin sulfonates, dialkyl sulfosuccinates, alkyl sulfates, alkyl polyester sulfates, alkyl phosphates, very long-chain alkylbenzene sulfonates, for example, SDS, LAS, sodium cholate, sodium lauryl sulfate, etc.), cationic (fatty amines and their salts, quaternary ammonium salts, polyethoxylated fatty amines), nonionic (polyethoxylated alkylphenols, polyethoxylated fatty alcohols, polyethoxylated fatty acids, alkanoamines or condensates of alkanoamines, such as alphol, nonylphenol, etc.), and amphoteric (n-alkylbetaines, n-alkyl sulfobetaines, alkyl imidazolines, n-alkyl-β-aminopropionic acid, etc.).

The invention is illustrated by the following examples:

EXAMPLE 1

Starting with a culture of Haloferax Mediterranei ATCC 33500 (the ATCC number refers to the culture number filed in the American Type Culture Collection, Bethesda, Md., United States). The properties of this microorganism as a producer of PHA are described in U.S. Pat. No. 890,347. A 500 ml volume of culture, containing 10 g/l of biomass, of which 6 g/l are PHA, is centrifuged at 600 rpm for 15 min, yielding a concentrated sediment, from which the supernatant is eliminated by decanting.

Then, the sediment is resuspended in 500 ml of distilled water containing 0.1% of SDS. The sediment is resuspended by intense agitation in the suspension medium; after obtaining a homogeneous suspension, one waits until the turbidity disappears—which occurs between 1 and 20 min.

The suspension is centrifuged at 2,000 rpm for 5 min, yielding a whitish, compact sediment. The supernatant is decanted and [the sediment] is resuspended in 500 ml of water with SDS (0.1%), centrifuged as in the previous step, and resuspended in distilled water (500 ml), and again centrifuged.

The water is removed by decanting, and the resultant paste is dried in an oven, by spraying, into a fluidized bed in a current of air at 70° C. for approximately 2 hr, yielding some 3 g of PHA with a purity level of 98.99%.

EXAMPLE 2

The cells are separated by centrifugation analogous to the previous case and resuspended in distilled water by intense agitation in a laboratory triturator. The suspension is heated at 65° C. for 20 min. After this step, [the suspension] is centrifuged at 200 rpm for 5 min, followed by repetition of all the steps of the previous example as to the treatment with water, detergents, and successive centrifugations. A product is obtained with a yield of 97 to 99% and a purity of 98.99%.

Example 3

Different proportions of water and detergent were tested relative to the PHA in multiple contacts with mixtures of water and detergents new in each step (washing in a single step would require some very large quantities of water and detergents). For example, a liter of culture medium containing in turn 10 g/l of biomass, of which 5 to 6 g/l are PHA, was subjected to a process similar to that of Example 1, with a cell-rupturing step to treat the concentrate with dissolution by water without salts and detergents (this treatment is optional, if not performed, worse yields are obtained). After centrifugation at 8,000 rpm for 20 min, the resultant suspension was divided into three parts. One of them was processed with 3×250 ml of SDS solution in water at 0.2%, another with 3 ×125 ml of the same solution, and the last with 3×75 ml of said solution. The processing ended with a washing with water to eliminate the detergent; after that, drying was performed in an oven or in a fluidized bed in a current of air at 70° C. for 2 hours. The yield in all cases was greater than 95% and the purity, determined by dissolving the PHA sample and weighing the insoluble residue was from 98 to 99% in the first case, from 90 to 91% in the second case, and from 87 to 90% in the third case, respectively.

EXAMPLE 4

The cell lysis step is performed before the washing in countercurrent because this method improves the yield. In the lysis step, it is possible to use a detergent and also a cation sequestering or complexing agent (e.g., ethylenediaminetetraacetic acid, EDTA) to improve purity. For example, the purity obtained in the case of processing the concentrate obtained as in Example 1 with 3×500 ml of water with SDS at 2% or with 3×500 ml of water with SDS and ethylenediaminetetraacetic acid (EDTA) 0.6 mM was 78.8% compared to 92% in the second case.

EXAMPLE 5

Another example of the action of agents which favor the lysis of bacteria before beginning the washing in countercurrent is the use of a bile salt, such as taurocholic acid, which enables reducing consumption of water and also of detergent without any detectable reduction in purity. For example, the purity [sic: product] obtained by processing a liter of medium is centrifuged at 8,000 rpm for 20 minutes, the resultant sediment is washed with 125 ml of SDS 0.2%, 6 mM of taurocholic acid, then is washed with 125 ml of SDS 0.2%, yielding a final product with a purity of 96 to 97%.

EXAMPLE 6

3 1 of medium containing 3 g/l of PHA were processed. One liter was treated with 3×500 ml of SDS at 0.2%, the second with 500 ml of SDS at 0.2% and 2×500 ml of SDS at 0.1%, and the third with 3×500 ml of SDS at 0.1%. In all cases the previous washing (lysis step) was performed with SDS and EDTA 0.6 mM. The final purities were 91.9% 76.9% and 59.3% respectively.

EXAMPLE 7

Washing in countercurrent. A test was performed on the sediment resulting from a treatment similar to that described in Example 1, but using EDTA as in Example 5. Treatment was carried out with 150 ml of water with SDS at 0.2% in a continuous countercurrent battery, with three steps. The purity obtained was 97%.

We claim

1. A method for extracting polyhydroxyalkanoates, comprising:

(a) providing halophilic bacteria containing polyhydroxyalkanoates, the bacteria being cultured in a medium which prevents rupture of the bacteria;

(b) surrounding the bacteria in a medium comprising a bile salt and having a concentration of NaCl low enough to lyse the bacteria and cause the polyhydroxyalkanoates to be released into the medium; and (c) isolating the released polyhydroxyalkanoates.

2. A method as claimed in claim 1, wherein the halophilic bacteria are halobacteria.

3. A method as claimed in claim 1, wherein the halophilic bacteria are Haloferax Mediterranei.

4. A method as claimed in claim 1, wherein the medium in step (b) further comprises a detergent.

5. A method as claimed in claim 4, wherein the medium in step (b) further comprises a cation complexing agent.

6. A method as claimed in claim 4, wherein the detergent is selected from the group consisting of anionic detergents, cationic detergents, nonionic detergents, and amphoteric detergents.

7. A method as claimed in claim 4, wherein the detergent is sodium dodecyl sulfate.

8. A method as claimed in claim 1, wherein step (b) further comprises:

washing the isolated polyhydroxyalkanoates in water and a detergent selected from the group consisting of anionic detergents, cationic detergents, nonionic detergents, and amphoteric detergents, thereby reducing the lipid and protein contamination of the isolated polyhydroxyalkanoates.

9. A method as claimed in claim 4 wherein the detergent is selected from the group consisting of sodium dodecyl sulfate, linear alkylbenzene sulfonate, sodium cholate, alphol, nonylphenol, the method further comprising the use of any cation complexing agent of the type ethylenediaminetetraacetic acid, at low concentrations of 0 to 1.5%, to facilitate the lysis of the bacteria and to increase the yield and purity of the polyhydroxyalkanoate obtained.

10. A method as claimed in claim 1 wherein a process selected from trituration, agitation, vibration, decompression and heating is used to facilitate the lysis of the cells.

11. A method as claimed in claim 4 wherein the detergent is used for washing and elimination of lipids and proteins from the resultant polyhydroxyalkanoate.

12. The procedure according to claim 9, characterized in that a detergent of the type described is used for washing and elimination of lipids and proteins from the resultant polyhydroxyalkanoate.

13. A method for extracting polyhydroxyalkanoates from halobacteria containing polyhydroxyalkanoates, the method comprising:

(a) surrounding the bacteria in a medium comprising a bile salt and having a concentration of NaCl low enough and a concentration of magnesium 2+ ion low enough to lyse the bacteria and cause the polyhydroxyalkanoates to be released into the medium; and (b) isolating the released polyhydroxyalkanoates.

14. A method as claimed in claim 3, wherein the concentration of NaCl in the medium is less than 0.5% and the concentration of the magnesium 2+ ion in the medium is less than 0.1%.

15. A method as claimed in claim 8 wherein the washing is performed continuously.

16. A method as claimed in claim 15 wherein a final washing step is performed with water to eliminate the detergent.

17. A method as claimed in claim 8 wherein at least one from the group consisting of sodium dodecyl sulfate, from 0 to 2%, ethylenediaminetetraacetic acid, from 0 to 6 mM, sodium deoxycholate, from 0 to 6 mM, is used to facilitate the lysis step; and sodium dodecyl sulfate, from 0 to 3%, is used for washing in a countercurrent process in at least one step, with a ratio of washing water to polyhydroxyalkanoate of up to 200:1, in which it is possible to obtain yields greater than 98% with purity better than 98%.

* * * * *